United States Patent [19]

Rentzea et al.

[11] 4,328,028

[45] May 4, 1982

[54] PLANT GROWTH REGULATORS

[75] Inventors: Costin Rentzea, Heidelberg; Johann Jung, Limburgerhof; Hubert Sauter, Ludwigshafen; Gerd Heilen, Frankenthal; Bernd Zeeh, Ludwigshafen, all of Fed. Rep. of Germany

[73] Assignee: BASF Aktiengesellschaft, Fed. Rep. of Germany

[21] Appl. No.: 936,741

[22] Filed: Aug. 25, 1978

[30] Foreign Application Priority Data

Sep. 1, 1977 [DE] Fed. Rep. of Germany ....... 2739352

[51] Int. Cl.³ .................... A01N 43/64; A01N 43/50
[52] U.S. Cl. .......................................... 71/76; 71/90; 71/92
[58] Field of Search ............................... 71/92, 90, 76

[56] References Cited

U.S. PATENT DOCUMENTS

| | | | |
|---|---|---|---|
| 4,113,465 | 9/1978 | Shephard et al. | 71/76 |
| 4,124,369 | 11/1978 | Kramer et al. | 71/92 |
| 4,140,518 | 2/1979 | Nurssen et al. | 71/92 |
| 4,181,518 | 1/1980 | Shephard et al. | 71/76 |
| 4,217,129 | 8/1980 | Shephard et al. | 71/76 |

FOREIGN PATENT DOCUMENTS

| | | |
|---|---|---|
| 2634511 | 2/1978 | Fed. Rep. of Germany . |
| 2656728 | 6/1978 | Fed. Rep. of Germany . |

OTHER PUBLICATIONS

Tolbert, J. Biol. Chem. vol. 235, No. 2 (1960) pp. 475-479.

*Primary Examiner*—Catherine L. Mills
*Attorney, Agent, or Firm*—Keil & Witherspoon

[57] ABSTRACT

Agents for regulating plant growth containing ketone derivatives bearing an azolyl radical in the β-position to the keto group, and a process for regulating plant growth with these compounds.

4 Claims, No Drawings

PLANT GROWTH REGULATORS

The present invention relates to agents for regulating plant growth containing β-azolylketones or their salts or metal complexes, and the use of these compounds for regulating plant growth.

The use of nitrogenous compounds such as chlorocholine chloride (CCC) for regulating plant growth has been disclosed (J. Biol. Chem., 235, 475 (1960)).

Plant growth regulators cause a variety of plant responses, e.g., reduction in growth height; inducing earlier germination, budding or flowering; resistance to freeze injury; promotion or inhibition of branching; defoliation; and fruit abscission, facilitating for instance harvesting. Of considerable economic interest is particularly the prevention of lodging in cereals before harvesting.

When the prior art ammonium salt mentioned above is used for regulating plant growth for instance in cereals in which a more compact growth is desired in order to prevent lodging, the action is often insufficient.

We have now found that agents for regulating plant growth which contain β-azolylketones of the formula $$R^1-CO-CH_2-\underset{\underset{Az}{|}}{CH}-R^2, \qquad I$$

where $R^1$ and $R^2$ are identical or different and each denotes alkyl, cycloalkyl, alkoxyalkyl which may be a ring, nitroalkyl, alkenyl of a maximum of 8 carbon atoms, furyl, thienyl, pyridyl, naphthyl, unsubstituted phenyl, or phenyl substituted by fluorine, chlorine, bromine, alkyl, alkoxy, trifluoromethyl or nitro, and Az denotes an imidazolyl, 1,2,4-triazolyl or 1,2,3-triazolyl radical, or salts or metal complexes thereof, have an excellent growth-regulating action and are excellently tolerated by crop plants.

$R^1$ denotes for example tert-butyl, furanyl, thiophenyl, pyridyl, α- and β-naphthyl, phenyl, p-fluorophenyl, p-chlorophenyl, m- and p-bromophenyl, 2,4-dichlorophenyl, p-tolyl or p-methoxyphenyl.

Examples of meanings for $R^2$ are tert-butyl, furanyl, pyridyl, o-methoxyphenyl or 2-methyl-4-chlorophenyl.

Examples of salts are hydrochlorides, bromides, sulfates, nitrates, phosphates, oxalates or dodecylbenzene sulfonates. As the activity of the salts is attributable to the cation, any anion may be selected.

Metal complexes are compounds of the formula $$[Me(R^1-\overset{\overset{O}{\|}}{C}-CH_2-\underset{\underset{Az}{|}}{CH}-R^2)_m]X_n, \qquad II$$

where $R^1$, $R^2$ and Az have the above meanings, Me denotes a metal, e.g., copper, zinc, tin, manganese, iron, cobalt or nickel, X denotes the anion of an inorganic acid, m denotes one of the integers 1, 2, 3 and 4, and n denotes one of the integers 1, 2, 3 and 4.

We have also found that β-azolylketones of the formula I and salts thereof are obtained by reaction of α,β-unsaturated ketones of the formula $$R^1-CO-CH=CH-R^2 \qquad III,$$

where $R^1$ and $R^2$ have the above meanings, with imidazole, 1,2,4-triazole or 1,2,3-triazole, in the presence or absence of a basic catalyst and of a diluent.

This method of manufacture is preferred. The compounds of the formula I are also obtained by reaction of α-haloketones of the formula IV or β-haloketones of the formula V $$R^1-CO-\underset{\underset{Y}{|}}{CH}-CH_2-R^2 \qquad IV$$

$$R^1-CO-CH_2-\underset{\underset{Y}{|}}{CH}-R^2, \qquad V$$

where $R^1$ and $R^2$ have the above meanings and Y denotes halogen (Cl), with imidazole, 1,2,4-triazole or 1,2,3-triazole, in the presence or absence of an acid binder and of a diluent. The reaction with the α-haloketone is preferably carried out in the presence of an acid binder; hydrogen halide is eliminated, giving an α,β-unsaturated ketone which is reacted to the β-azolylketone in the manner described above. From the compounds of the formula I obtained by the above processes, the salts can be prepared with acids.

We have further found that the metal complexes of the formula II are obtained by reaction of β-azolylketones of the formula I with metal salts of the formula $$MeX_n \cdot aH_2O \qquad VI,$$

where Me, X and n have the above meanings and a denotes one of the integers 0, 1, 2, 3 and 4, in the presence of a solvent.

The reaction of α,β-unsaturated ketones with imidazole, 1,2,4-triazole or 1,2,3-triazole by the process described above is advantageously carried out without a diluent or in an indifferent solvent, e.g., methanol, ethanol, isopropanol, n-butanol, tetrahydrofuran, dioxane, toluene, xylene, and dimethylformamide, at from about 0° to 100° C., preferably from 20° to 50° C. It is advantageous to add a catalytic amount of an alkaline compound, e.g., sodium hydroxide, potassium hydroxide, triethylamine and N,N-dimethylcyclohexylamine.

Compounds III used as starting materials are disclosed in the literature and may be manufactured conventionally from ketones and aldehydes.

The metal salts employed for the manufacture of the metal complexes are defined in general form by formula VI, where Me preferably denotes metals or subgroups I, II and IV to VIII, or of main groups II and IV of the periodic system, especially copper, zinc, tin, manganese, iron, cobalt and nickel.

The metal salts of the formula IV are generally known, easily accessible compounds.

Suitable solvents for the manufacture of the metal complexes of the formula II are all those miscible with water, preferably methanol, ethanol, isopropanol, acetone, tetrahydrofuran and dioxane. The temperatures employed are in general from 0° to 100° C., preferably from 10° to 35° C.

EXAMPLE 1

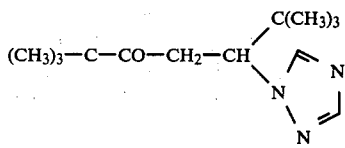

16.8 g of 2,2,6,6-tetramethylhepten-3-one-5, 11 g of 1,2,4-trizaole and 0.1 g of potassium hydroxide are dissolved in 100 ml of dioxane, and the whole is stirred for 4 hours at 40° C. The solvent is then distilled off in vacuo, the residue is dissolved in 200 ml of ether and the organic solution washed twice (75 ml each time) with water. The organic phase is then dried over sodium sulfate, filtered and concentrated. The residue is washed at 10° C. with 50 ml of petroleum ether, suction filtered and dried.

There is obtained 21.8 g (92% of theory) of 3-(1,2,4-triazolyl-(1))-2,2,6,6-tetramethylheptan-5-one as white analytically pure crystals having a melting point of 98° to 99° C.

EXAMPLE 2

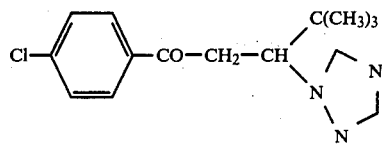

22.2 g of 1-(4'-chlorophenyl)-4,4-dimethylpenten-2-one-1, 11 g of 1,2,4-triazole and 0.3 g of potassium hydroxide are dissolved in 200 ml of ethanol and the whole is stirred for 6 hours at 50° C. The diluent is then distilled off in vacuo, the residue is dissolved in 250 ml of methylene chloride, and the organic phase is washed twice (100 ml each time) with water. The organic phase is then dried over sodium sulfate, filtered and concentrated. The residue is stirred with 75 ml of isooctane, suction filtered and dried.

There is obtained 27.7 g (95% of theory) of 3-(1,2,4-triazolyl-(1))-1-(4'-chlorophenyl)-4,4-dimethylpentan-1-one as white crystals; m.p.: 113° to 115° C. The corresponding hydrochloride melts at 156° to 157° C. The compounds listed in Table 1 are prepared analogously.

TABLE 1

$$R^1-CO-CH_2-CH\genfrac{}{}{0pt}{}{R^2}{Az}$$

| Ex. no. | $R^1$ | $R^2$ | Az | m.p. °C. | m.p. °C. (hydrochloride) |
|---|---|---|---|---|---|
| 3 | (furyl) | $(CH_3)_3C-$ | (triazolyl) | 104–106 | |
| 4 | (thienyl) | $(CH_3)_3C-$ | (triazolyl) | 125–127 | |
| 5 | $(CH_3)_3C-$ | (pyridyl) | (triazolyl) | 79 | |
| 6 | (naphthyl) | $(CH_3)_3C-$ | (triazolyl) | 136–138 | 144–145 |
| 7 | $C_6H_5-$ | $(CH_3)_3C-$ | (triazolyl) | 160–162 | 206–208 |
| 8 | $F-C_6H_4-$ | $(CH_3)_3C-$ | (triazolyl) | 100–102 | 131–132 |
| 9 | $Cl-C_6H_4-$ | $(CH_3)_3C-$ | (triazolyl) | 130–132 | |

TABLE 1-continued $$R^1-CO-CH_2-CH\genfrac{}{}{0pt}{}{R^2}{Az}$$

| No. | R¹ | R² | Az | mp (°C) | mp (°C) salt |
|---|---|---|---|---|---|
| 10 | 4-Cl-C₆H₄- | (CH₃)₃C- | 1,2,4-triazol-1-yl | 121–124 | 133–135 |
| 11 | 3-Br-C₆H₄- | (CH₃)₃C- | 1,2,4-triazol-1-yl | 114–116 | |
| 12 | 4-Br-C₆H₄- | (CH₃)₃C- | 1,2,4-triazol-1-yl | 140–142 | 176–178 |
| 13 | 3,4-Cl₂-C₆H₃- | (CH₃)₃C- | 1,2,4-triazol-1-yl | 70–72 | 112–114 |
| 14 | 4-CH₃-C₆H₄- | (CH₃)₃C- | 1,2,4-triazol-1-yl | 128–130 | 142–143 |
| 15 | (CH₃)₃C- | 4-Cl-2-CH₃-C₆H₃- | 1,2,4-triazol-1-yl | 50–52 | |
| 16 | 4-CH₃O-C₆H₄- | 2-OCH₃-C₆H₄- | 1,2,4-triazol-1-yl | 135 | |
| 17 | (CH₃)₃C- | 2-OCH₃-C₆H₄- | 1,2,4-triazol-1-yl | 92–95 | |
| 18 | (CH₃)₂CH- | naphthyl | 1,2,4-triazol-1-yl | | 159–161 |
| 19 | (CH₃)₂CH-CH₂- | naphthyl | 1,2,4-triazol-1-yl | | 167–169 |
| 20 | 4-Cl-C₆H₄- | (CH₃)₂CH-CH₂- | 1,2,4-triazol-1-yl | | 168–170 |
| 21 | 4-Cl-C₆H₄- | (CH₃)₂CH- | " | | 108–110 |
| 22 | C₆H₅- | (CH₃)₂CH-CH₂- | " | 126–128 | |
| 23 | 4-Cl-C₆H₄- | H₂C=CH-CH₂-C(CH₃)₂-CH₃ | " | | 155 |
| 24 | 4-Cl-C₆H₄- | (C₂H₅)₂CH- | " | | 124–125 |

TABLE 1-continued $$R^1-CO-CH_2-CH\genfrac{}{}{0pt}{}{R^2}{Az}$$

| Ex. no. | R¹ | R² | Az | m.p. (°C.) |
|---|---|---|---|---|
| 25 |  | 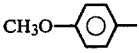 CH₃O— | " | 171–174 |
| 26 | 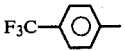 F₃C— |  | " | 114–116 |
| 27 |  | 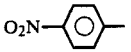 O₂N— | " | 193–195 |
| 28 |  O₂N—C(CH₃)₂— |  Cl— | " | 126–128, 170–172 |
| 29 | 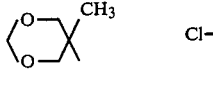 | 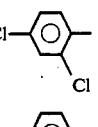 Cl—,Cl | " | 90–92 |
| 30 | CH₃— |  Cl—,Cl | " | 114–117 |
| 31 | (CH₃)₃C |  pyridyl |  triazolyl | 88–90 |
| 32 | (CH₃)₃C | 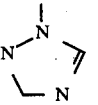 Cl-phenyl | " | IR (film): 2981, 1700, 1470, 1271, 1133, −1003, 739, 678, 658 cm⁻¹ |
| 33 | (CH₃)₃C |  Cl,Cl-phenyl | " | IR (film): 2982, 1703, 1431, 1363, 1273, −1136, 1008, 779, 676 cm⁻¹ |
| 34 | (CH₃)₃C |  O₂N-phenyl | " | 81–83 |
| 35 |  OCH₃-phenyl | 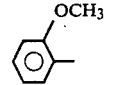 H₃CO-phenyl | " | 11–114 |
| 36 |  H₃CO-phenyl | 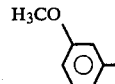 H₃CO-phenyl | " | 114–116 |
| 37 |  H₃C—phenyl | 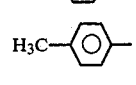 H₃CO-phenyl | " | 99–101 |
| 38 |  H₃CO—phenyl | 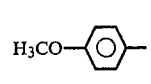 | " | 128–129 |
| 39 |  Cl—phenyl | n-propyl | " | 76–78 |
| 40 | 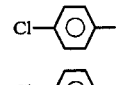 Cl—phenyl | n-butyl | " | 94–96 |
| 41 | (CH₃)₃C | i-propyl | " | 108–110 |
| 42 | (CH₃)₃C | n-butyl | " | IR (film): 2975, 2930, 1705, 1365, −1268, 1132, 1003, 670 cm⁻¹ |
| 43 | (CH₃)₃C | 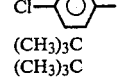 pyridyl | " | 71–73 |

TABLE 1-continued $R^1-CO-CH_2-CH{<}^{R^2}_{Az}$

| # | R¹ | R² | Az | m.p./IR |
|---|---|---|---|---|
| 44 |  (2-OCH₃-phenyl) | t-butyl | " | 75–77 |
| 45 |  (4-methylphenyl) | t-butyl | " | 81–83 |
| 46 |  (2-OCH₃-phenyl) |  (H₃CO-phenyl) | " | 125–126 |
| 47 | H₃CO—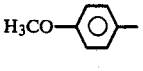 |  (naphthyl) | " | 126–128 |
| 48 | (CH₃)₃C | 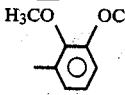 (H₃CO, OCH₃-phenyl) | " | IR (film): 2960, 1702, 1582, 1473, −1267, 1061, 1000, 745 cm⁻¹ |
| 49 | 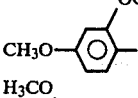 (CH₃O, OCH₃-phenyl) | t-butyl | " | 105–107 |
| 50 | H₃CO—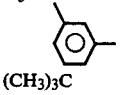 | t-butyl | " | 64–66 |
| 51 | (CH₃)₃C | F— | " | 89–91 |
| 52 | H₃CO—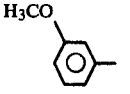 | t-butyl | " | 125–126 |
| 53 | 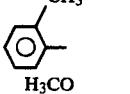 (CH₃-phenyl) | t-butyl | " | 70–72 |
| 54 | 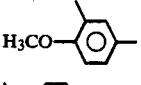 (H₃CO, H₃CO-phenyl) | t-butyl | " | 150–152 |
| 55 |  (isopropyl-phenyl) | t-butyl | " | 135–137 |
| 56 | ethyl | t-butyl | " | 48–50 |
| 57 | methyl | 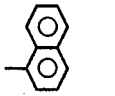 (naphthyl) | " | 123–124 |
| 58 | n-propyl | t-butyl | " | IR (film): 2952, 2860, 1708, 1495, 1363, 1267, 1132, 1003, 675 cm⁻¹ |
| 59 | n-Pentyl | t-butyl | " | IR (film): 2945, 2920, 2859, 1707, 1496, 1363, 1267, 1133, 1003, 675 cm⁻¹ |
| 60 | n-hexyl | t-butyl | " | IR (film): 2943, 2919, 2859, 1707, 1494, 1363, 1263, 1133, 1002, 675 cm⁻¹ |
| 61 | n-butyl | t-butyl | " | IR (film): 2946, 2860, 1706, 1365, 1268, 1132, 1003, 676 cm⁻¹ |
| 62 | 4-methyl-pentyl-(1) | t-butyl | " | IR (film): 2945, 2860, 1710, 1497, 1363, 1269, 1134, 1003, 676 cm⁻¹ |

EXAMPLE 63

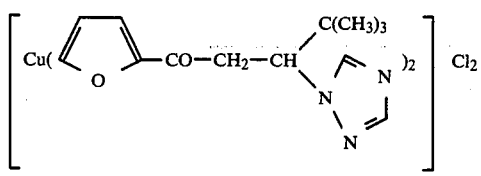

8.5 g of copper dichloride (CuCl$_2$.2H$_2$O) is dissolved in 100 ml of ethanol; while stirring thoroughly, this solution is slowly dripped into a solution of 24.7 g of 3-(1,2,4-triazolyl-(1))-1-(2'-furyl)-4,4-dimethylpentan-1-one in 150 ml of ethanol. The mixture is stirred for a further 3 hours at room temperature. The turquoise crystals are filtered off and washed with 25 ml of ice-cold ethanol. There is obtained 30 g (95% of theory) of bis-(3-(1,2,4-triazolyl-(1))-1-(2'-furyl)-4,4-dimethylpentan-1-one)-copper(II) chloride; m.p. 123°–124° C.

EXAMPLE 64

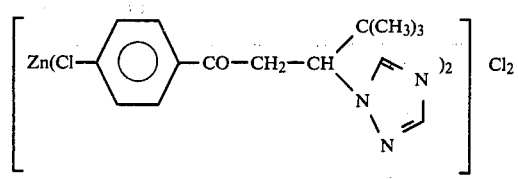

6.8 g of ZnCl$_2$ is dissolved in 50 ml of ethanol; while stirring, this solution is slowly dripped into a solution of 29.1 g of 3-(1,2,4-triazolyl-(1))-1-(4'-chlorophenyl)-4,4-dimethylpentan-1-one in 200 ml of ethanol. After the mixture has been stirred for 2 hours at room temperature, the colorless crystals are filtered off and washed with 25 ml of ice-cold ethanol. There is obtained 26 g (80% of theory) of bis-(3-(1,2,4-triazolyl-(1))-1-(4'-chlorophenyl)-4,4-dimethylpentan-1-one)-zinc(II) chloride; m.p.: 149°–152° C.

The metal complexes listed in Table 2 may be prepared in the same manner.

TABLE 2

$$\left[ Me(R^1-CO-CH_2-CH{<}^{R^2}_{Az})_m \right] Y_n$$

| Ex. no. | Me | R$^1$ | R$^2$ | Az | Y | n | m | m.p. °C. |
|---|---|---|---|---|---|---|---|---|
| 65 | Cu | 2-thienyl | (CH$_3$)$_3$C— | 1,2,4-triazolyl | Cl | 2 | 2 | 208–210 |
| 66 | Cu | (CH$_3$)$_3$C— | 2-piperidyl | 1,2,4-triazolyl | Cl | 2 | 1 | 178 |
| 67 | Cu | 2-naphthyl | (CH$_3$)$_3$C— | 1,2,4-triazolyl | Cl | 2 | 2 | 196–198 |
| 68 | Cu | 4-Cl-phenyl | (CH$_3$)$_3$C— | 1,2,4-triazolyl | Cl | 2 | 2 | 215–218 |
| 69 | Cu | 4-Cl-phenyl | (CH$_3$)$_2$CH— | 1,2,4-triazolyl | Cl | 2 | 2 | 195–197 |
| 70 | Cu | 3,4-diCl-phenyl | (CH$_3$)$_3$C— | 1,2,4-triazolyl | Cl | 2 | 2 | 155–157 |
| 71 | Cu | 4-CH$_3$-phenyl | (CH$_3$)$_3$C— | 1,2,4-triazolyl | Cl | 2 | 2 | 213–215 |
| 72 | Cu | 4-CH$_3$O-phenyl | 2-OCH$_3$-phenyl | 1,2,4-triazolyl | Cl | 2 | 2 | 161 |

TABLE 2-continued $$\left[ Me(R^1-CO-CH_2-CH\genfrac{}{}{0pt}{}{R^2}{Az})_m Y_n \right]$$

| Ex. no. | Me | R¹ | R² | Az | Y | n | m | m.p. °C. |
|---|---|---|---|---|---|---|---|---|
| 73 | Cu | (CH₃)₃C— | 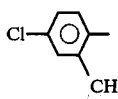 |  | Cl | 2 | 2 | 173–175 |

The β-azolylketones according to the invention are excellently suited for regulating growth in numerous plants; the effect is especially manifested in a reduction in growth height. The action of these growth regulators and tolerance of them by crop plants are better than in the case of prior art growth regulators.

Compounds of formulae I and II may also be applied together with other crop protection agents, e.g., herbicides, insecticides and—especially—fungicides. Combined application with fertilizers, especially admixture with ureas, is advantageous in practice.

The growth-regulating action is particularly apparent in cereals, e.g., wheat, rye, barley, rice and oats, but also in dicotyledons (e.g., sunflowers, tomatoes, grapes, cotton and rape) and various ornamentals such as poinsettias and hibiscus. The treated plants do not grow as high as, and generally are more compact than, untreated plants; furthermore, the leaves take on a darker coloration.

As a result of the excellent tolerance by crop plants, the application rate may be varied to a considerable extent; generally, from 0.05 to 12 kg, preferably 0.1 to 4 kg, of active ingredient is used per hectare.

Examples of β-azolylketones according to the invention are as follows:

3-(1,2,4-triazolyl-(1))-2,2,6,6-tetramethylheptan-5-one
3-(1,2,4-triazolyl-(1))-1-(2'-furyl)-4,4-dimethylpentan-1-one
3-(1,2,4-triazolyl-(1))-1-(2'-tienyl)-4,4-dimethylpentan-1-one
1-(1,2,4-triazolyl-(1))-1-(2'-pyridyl)-4,4-dimethylpentan-3-one
3-(1,2,4-triazolyl-(1))-1-(1-naphthyl)-4,4-dimethylpentan-1-one and its hydrochloride
3-(1,2,4-triazolyl-(1))-1-phenyl-4,4-dimethylpentan-1-one
3-(1,2,4-triazolyl-(1))-1-(4'-fluorophenyl)-4,4-dimethylpentan-1-one and its hydrochloride
3-(1,2,3-triazolyl-(1))-1-(4'-chlorophenyl)-4,4-dimethylpentan-1-one and its hydrochloride
3-(1,2,3-triazolyl-(1))-1-(4'-chlorophenyl)-4,4-dimethylpentan-1-one
3-(1-imidazolyl)-1-(4'-chlorophenyl)-4,4-dimethylpentan-1-one and its hydrochloride
3-(1,2,4-triazolyl-(1))-1-(3'-bromophenyl)-4,4-dimethylpentan-1-one
3-(1,2,4-triazolyl-(1))-1-(4'-bromophenyl)-4,4-dimethylpentan-1-one
3-(1,2,4-triazolyl-(1))-1-(2',4'-dichlorophenyl)-4,4-dimethylpentan-1-one and its hydrochloride
3-(1,2,4-triazolyl-(1))-1-(4'-methylphenyl)-4,4-dimethylpentan-1-one and its hydrochloride
1-(1,2,4-triazolyl-(1))-1-(2'-methyl-4'-chlorophenyl)-4,4-dimethylpentan-3-one
3-(1,2,3-triazolyl-(1))-3-(2'-methoxyphenyl)-1-(4'-methoxyphenyl)propan-1-one
1-(1,2,4-triazolyl-(1))-1-(2'-methoxyphenyl)-4,4-dimethylpentan-3-one.

Examples of metal complexes according to the invention are as follows:

bis-(3-(1,2,4-triazolyl-(1))-1-(2'-furyl)-4,4-dimethylpentan-1-one)-copper(II) chloride
bis-(3-(1,2,4-triazolyl-(1))-1-(2'-thienyl)-4,4-dimethylpentan-1-one)-copper(II) chloride
(1-(1,2,4-triazolyl-(1))-1-(2'-pyridyl)-4,4-dimethylpentan-3-one)-copper(II) chloride
bis-(3-(1,2,4-triazolyl-(1-))-1-(1'-naphthyl)-4,4-dimethylpentan-1-one)-copper(II) chloride
bis-(3-(1,2,4-triazolyl-(1))-1-(4'-chlorophenyl)-4,4-dimethylpentan-1-one)-copper(II) chloride
bis-(3-(1,2,4-triazolyl-(1))-1-(4'-chlorophenyl)-4,4-dimethylpentan-1-one-zinc(II) chloride
bis-(3-(1,2,4-triazolyl-(1))-1-(4'-chlorophenyl)-4-methylpentan-1-one-copper(II) chloride
bis-(3-(1,2,4-triazolyl-(1))-1-(2',4'-dichlorophenyl)-4,4-dimethylpentan-1-one)-copper(II) chloride
bis-(3-(1,2,4-triazolyl-(1))-1-(4'-methylphenyl)-4,4-dimethylpentan-1-one)-copper(II) chloride
bis-(3-(1,2,4-triazolyl-(1))-3-(2'-methoxyphenyl)-1-(4'-methoxyphenyl)-propan-1-one)-copper(II) chloride
bis-(1-(1,2,4-triazolyl-(1))-1-(2'-methyl-4'-chlorophenyl)-4,4-dimethylpentan-3-one)-copper(II) chloride.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredients according to the invention.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as toluene, xylene, paraffin, tetrahydronaphthalene, alkylated naphthalenes and their derivatives, alcohols (e.g., methanol, butanol), amines (e.g., ethanolamine, dimethylformamide), and water; carriers such as natural rock flours (e.g. highly disperse silicic acid, silicates); emulsifiers such as non-ionogenic and anionic emulsifiers (e.g., polyoxyethylene fatty alcohol ethers, alkyl sulfonates and aryl sulfonates) and dispersants such as lignin, sulfite waste liquors and methyl cellulose, are suitable.

The formulations contain from 0.1 to 95, and preferably 0.5 to 90, % by weight of active ingredient.

The agents according to the invention should be applied in a favorable period, the exact determination of which depends on geographic, climatic and vegetative conditions.

In the following examples, the effect on growth height is described, without excluding the possibility of other responses as discussed above.

EXAMPLE A

Greenhouse experiments—Neubauer system

In the greenhouse, seeds of the test plants were sown in a peat substrate provided with sufficient nutrients, in plastic pots having a diameter of 12.5 cm. The active ingredients were sprayed, as an aqueous solution or dispersion at various rates, directly onto the surface of the soil on the day the seeds were sown. During the 18 day growth period, the plants treated with the agents according to the invention exhibited a considerably reduced growth height compared with the untreated control, a fact which was subsequently confirmed by measurements of the height. 100 plants were measured from each series treated. The action of chlorocholine chloride (N-2-chloroethyl-N,N,N-trimethylammonium chloride=CCC), the prior art compound used for comparison purposes, was surpassed.

TABLE 3

| Influence on the growth height of wheat; soil treatment | | | |
|---|---|---|---|
| Compound | Appln. rate | Height | |
| Ex. no. | kg/ha | cm | relative |
| Control (untreated) | — | 30.0 | 100 |
| CCC | 3.0 | 21.5 | 71.7 |
| prior art | 12.0 | 19.5 | 65.0 |
| 2 | 3.0 | 18.5 | 61.7 |
|  | 12.0 | 11.5 | 38.3 |

TABLE 4

| Influence on the growth height of barley; soil treatment | | | |
|---|---|---|---|
| Compound | Appln. rate | Height | |
| Ex. no. | kg/ha | cm | relative |
| Control (untreated) | — | 32.0 | 100 |
| CCC | 3.0 | 26.0 | 81.3 |
| prior art | 12.0 | 23.5 | 73.4 |
| 2 | 3.0 | 22.0 | 68.8 |
|  | 12.0 | 16.0 | 50.0 |

TABLE 5

| Influence on the growth height of rape; soil treatment | | | |
|---|---|---|---|
| Compound | Appln. rate | Height | |
| Ex. no. | kg/ha | cm | relative |
| Control (untreated) | — | 17.0 | 100 |
| CCC | 3.0 | 17.0 | 100 |
| prior art | 12.0 | 17.0 | 100 |
| 2 | 3.0 | 15.0 | 88.2 |
|  | 12.0 | 13.0 | 76.5 |
| 14 | 3.0 | 16.0 | 94.1 |
|  | 12.0 | 14.0 | 82.4 |
| 4 | 3.0 | 15.0 | 88.2 |

TABLE 5-continued

| Influence on the growth height of rape; soil treatment | | | |
|---|---|---|---|
| Compound | Appln. rate | Height | |
| Ex. no. | kg/ha | cm | relative |
|  | 12.0 | 14.0 | 82.4 |

EXAMPLE B

Vegetation experiment—Mitscherlich system

To determine the action of the agents according to the invention on monocotyledons under conditions similar to those in the open, a vegetation experiment was carried out with spring barley in 10 liter vessels. The plants were grown in a sandy loam; as fertilizer, 1.5 g of N as ammonium nitrate and 1 g of $P_2O_5$ as secondary potassium phosphate where added to each vessel. After the barley had been sown, the active ingredient were applied to the surface of the soil as an aqueous dispersion. The comparative agent N-2-chloroethyl-N,N,N-trimethylammonium chloride (CCC) was, however, sprayed as an aqueous solution onto the leaves of the plants at a growth height of about 40 cm, as it is known of this compound that it becomes inactive in the soil over a fairly long vegetation period (longer than 4 weeks).

After the ears had developed, the plants treated with the active ingredient according to the invention had, at otherwise the same development stage, a considerably reduced growth height compared with the untreated control.

The action of the prior art compound CCC was able to be surpassed even at the lower application rate.

TABLE 6

| Influence on the growth height of barley; soil treatment | | | |
|---|---|---|---|
| Compound | Appln. rate | Height | |
| Ex. no. | kg/ha | cm | relative |
| Control (untreated) | — | 101.0 | 100 |
| CCC | 3.0 | 94.0 | 93.1 |
| prior art | 6.0 | 94.5 | 93.6 |
| 2 | 1.5 | 91.5 | 90.6 |
|  | 3.0 | 85.5 | 84.6 |

EXAMPLE 74

90 Parts by weight of compound 1 is mixed with 10 parts by weight of N-methyl-α-pyrrolidone. A mixture is obtained which is suitable for application in the form of very fine drops.

EXAMPLE 75

20 Parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 76

20 Parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 77

20 Parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 78

20 Parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 79

3 Parts by weight of compound 3 is intimately mixed with 97 parts by weight of particulate kaolin. A dust is obtained containing 3% by weight of the active ingredient.

EXAMPLE 80

30 Parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 81

40 Parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 82

20 Parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A process for regulating plant growth to effect a reduction in growth height, wherein the plants are treated with an effective amount of a compound of the formula

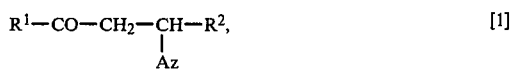

where
R$^1$ denotes furyl, thienyl, pyridyl, naphthyl, unsubstituted phenyl, or phenyl substituted by fluorine, chlorine, bromine, alkyl, alkoxy, trifluoromethyl or nitro,
R$^2$ denotes alkyl or cycloalkyl, and
Az denotes an imidazolyl, 1,2,4-triazolyl or 1,2,3-triazolyl radical, or a salt or metal complex thereof.

2. A process for regulating plant growth to effect a reduction in growth height according to claim 1, wherein the plants are treated with an effective amount of a metal complex of the formula

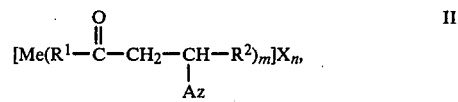

where Me denotes a metal selected from the group consisting of copper, zinc, tin, manganese, iron, cobalt and nickel; X denotes the anion of an inorganic acid, m denotes one of the integers 1, 2, 3 and 4; and n denotes one of the integers 1, 2, 3, and 4.

3. A process for regulating plant growth to effect a reduction in growth height according to claim 1, wherein R$^1$ denotes, furanyl, thiophenyl, pyridyl, α- and β-naphthyl, phenyl, p-fluorophenyl, p-chlorophenyl, m- and p-bromophenyl, 2,4-dichlorophenyl, p-tolyl or p-methoxyphenyl.

4. A process for regulating plant growth to effect a reduction in growth height according to claim 1, wherein R$^2$ denotes tert-butyl.

* * * * *